United States Patent [19]
Samson et al.

[11] Patent Number: 5,827,201
[45] Date of Patent: Oct. 27, 1998

[54] MICRO-BRAIDED GUIDEWIRE

[75] Inventors: Gene Samson, Milpitas; Kim Nguyen, San Jose, both of Calif.

[73] Assignee: Target Therapeutics, Inc., Fremont, Calif.

[21] Appl. No.: 686,887

[22] Filed: Jul. 26, 1996

[51] Int. Cl.[6] .................................................. A61B 5/00
[52] U.S. Cl. .......................................... 600/585; 604/281
[58] Field of Search ................................... 604/164, 280, 604/281, 95; 600/434, 585

[56]  References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 3,789,841 | 2/1974 | Antoshkiw . |
| 4,545,390 | 10/1985 | Leary . |
| 4,619,274 | 10/1986 | Morrison . |
| 4,665,906 | 5/1987 | Jervis . |
| 4,739,768 | 4/1988 | Engelson . |
| 4,763,647 | 8/1988 | Gambale . |
| 4,811,743 | 3/1989 | Stevens . |
| 4,925,445 | 5/1990 | Sakamoto et al. . |
| 4,969,890 | 11/1990 | Sugita et al. . |
| 4,984,581 | 1/1991 | Stice . |
| 4,991,602 | 2/1991 | Amplatz et al. . |
| 5,001,825 | 3/1991 | Halpern . |
| 5,069,217 | 12/1991 | Fleischhacker, Jr. . |
| 5,069,226 | 12/1991 | Yamauchi et al. . |
| 5,095,915 | 3/1992 | Engelson . |
| 5,171,383 | 12/1992 | Sagaye et al. . |
| 5,213,111 | 5/1993 | Cook et al. . |
| 5,228,453 | 7/1993 | Sepetka . |
| 5,238,004 | 8/1993 | Sahatjian et al. . |
| 5,259,393 | 11/1993 | Corso, Jr. et al. . |
| 5,353,808 | 10/1994 | Viera . |
| 5,356,388 | 10/1994 | Sepetka et al. . |
| 5,368,049 | 11/1994 | Raman et al. . |
| 5,402,799 | 4/1995 | Colon et al. . |
| 5,404,887 | 4/1995 | Prather . |
| 5,409,015 | 4/1995 | Palermo .................................. 600/585 |
| 5,433,200 | 7/1995 | Fleischhacer, Jr. . |
| 5,443,907 | 8/1995 | Slaikeu et al. . |
| 5,465,733 | 11/1995 | Hinohara et al. . |
| 5,488,959 | 2/1996 | Ales . |
| 5,538,513 | 7/1996 | Okajima . |

FOREIGN PATENT DOCUMENTS

| | | |
|---|---|---|
| 0359549 | 3/1990 | European Pat. Off. . |
| 0382974 | 8/1990 | European Pat. Off. . |
| 0515201 | 11/1992 | European Pat. Off. . |
| 0519604 | 12/1992 | European Pat. Off. . |
| WO 92/14508 | 9/1992 | WIPO . |

*Primary Examiner*—Scott M. Getzow
*Attorney, Agent, or Firm*—Morrison & Foerster LLP

[57] ABSTRACT

This is a composite guidewire for use in a catheter. It is used in medical procedures that involve accessing specifically targeted inner body areas without major surgery. The composite guidewire is especially useful for accessing peripheral soft tissue targets. The guidewire may be a multi-section guidewire assembly preferably having super-elastic alloy ribbon braided reinforcements along at least a portion of the core. The guidewire core may be of a stainless steel or a high elasticity metal alloy, preferably a Ni—Ti alloy. A variation of the guidewire also preferably includes a braid on the exterior of the core wire with an exterior polymeric coating to the most distal portion of the assembly and preferably assembled using adhesives such as epoxies.

65 Claims, 3 Drawing Sheets

MICRO-BRAIDED GUIDEWIRE

FIELD OF THE INVENTION

This invention is a surgical device. It is a composite guidewire for use in a catheter and is used for accessing a targeted site in a lumen system of a patient's body. The guidewire core may be of a stainless steel or a high elasticity metal alloy, preferably a Ni—Ti alloy. The composite guidewire assembly is especially useful for accessing peripheral or soft tissue targets. The invention includes multi-section guidewire assemblies preferably having super-elastic alloy ribbon braided reinforcements along at least a portion of the core. A variation of the inventive guidewire also preferably includes a braid on the exterior of the core wire with an exterior polymeric coating to the most distal portion of the assembly and preferably assembled using adhesives such as epoxies.

BACKGROUND OF THE INVENTION

Catheters are used increasingly as a means for delivering diagnostic and therapeutic agents to internal sites within the human body that can be accessed through the various lumen systems of the body, particularly through the vasculature. A catheter guidewire is used for guiding the catheter through the bends, loops, and branches forming the blood vessels within the body. One method of using a guidewire to direct the catheter through the tortuous paths of these systems of lumen involves the use of a torqueable guidewire which is directed as a unit from a body access point such as the femoral artery to the tissue region containing the target site. The guidewire is often slightly bent at its distal end, and may be guided by alternatively rotating and advancing the guidewire along the small vessel pathway to the desired target. Typically the guidewire and the catheter are advanced by alternatively moving the guidewire along a distance in the vessel pathway, holding the guidewire in place, and then advancing the catheter along the axis of the guidewire until it nears the distal portion of the guidewire.

The difficulty in accessing remote body regions, the body's periphery, or the soft tissues within the body such as the brain and the liver are apparent. The catheter and its attendant guidewire must be both flexible, allow the combination to follow the complicated path through the tissue, and yet stiff enough to allow the distal end of the catheter to be manipulated by the physician from the external access site. It is common that the catheter is as long as one meter or more.

The catheter guidewires used in guiding a catheter through the human vasculature have a number of variable flexibility constructions. For instance, U.S. Pat. Nos. 3,789,841; 4,545,390; and 4,619,274 show guidewires in which the distal end section of the wire is tapered along its length to allow great flexibility in that remote region of the guidewire. Distal tapering facilitates guidewire function, since the distal region is steered through turns with very small radii of curvature. The tapered section of the wire is often enclosed in a wire coil, typically of platinum, to increase the column strength of the tapered section without significant loss of flexibility in that region and also to increase the radial capacity of the guidewire to allow fine manipulation of the guidewire through the vasculature.

Another effective guidewire design is found in U.S. Pat. No. 5,095,915 which shows a guidewire having at least two sections. The distal portion is encased in an elongated polymer sleeve having axially spaced grooves to allow increased bending flexibility of the sleeve.

In addition to providing structural support for tapered core wire tips, polymer sleeves have been used to decrease contact friction between lumen walls and guidewires. U.S. Pat. No. 5,443,907, to Slaikeu et al., teaches a two layer polymer coating for a guidewire core wire which includes an inner layer of hydrophobic polymer bonded to an outer layer of hydrophilic polymer material. Such hydrophilic polymer coatings provide slippery surfaces which facilitate insertion and reduce vessel trauma.

Others have suggested the use of guidewires made of various super-elastic alloys in an attempt to achieve some of the noted functional desires.

U.S. Pat. No. 4,925,445, to Sakamoto et al., suggests the use of a two-portion guidewire having a body portion relatively high in rigidity and a distal end portion which is comparatively flexible. At least one portion of the body and the distal end portions is formed of super-elastic metallic materials. Although a number of materials are suggested, including Ni—Ti alloys of 49 to 58% (atm) nickel, the patent expresses a strong preference for Ni—Ti alloys in which the transformation between austenite and martensite is complete at a temperature of 10° C. or below. The reason given is that "for the guidewire to be useable in the human body, it must be in the range of 10° to 20° C. due to anesthesia at a low body temperature." The temperature of the human body is typically about 37° C.

Another document disclosing a guidewire using a metal alloy having the same composition as a Ni—Ti super-elastic alloy is WO91/15152 (to Sahatjian et al. and owned by Boston Scientific Corp.). That disclosure suggests a guidewire made of the precursor to the Ni—Ti elastic alloy. Super-elastic alloys of this type are typically made by drawing an ingot of the precursor alloy while simultaneously heating it. In the unstressed state at room temperature, such super-elastic materials occur in the austenitic crystalline phase and, upon application of stress, exhibit stress-induced austenite-martensite (SIM) crystalline transformations which produce nonlinear elastic behavior. The guidewires described in that published application, on the other hand, are said not to undergo heating during the drawing process. The wires are cold-drawn and great pain is taken to assure that the alloy is maintained well below 300° F. during each of the stages of its manufacture. This temperature control is maintained during the step of grinding the guidewire to form various of its tapered sections.

U.S. Pat. No. 4,665,906 suggests the use of stress-induced martensite (SIM) alloys as constituents in a variety of different medical devices. Such devices are said to include catheters and cannulas.

U.S. Pat. No. 4,969,890 to Sugita et al., suggests the production of a catheter having a main body fitted with a shape memory alloy member, and having a liquid injection means to supply a warming liquid to allow the shape memory alloy member to recover its original shape upon being warmed by the fluid.

U.S. Pat. No. 4,984,581, to Stice, suggests a guidewire having a core of a shape memory alloy, the guidewire using the two-way memory properties of the alloy to provide both tip-deflecting and rotational movement to the guidewire in response to a controlled thermal stimulus. The controlled thermal stimulus in this instance is provided through application of an RF alternating current. The alloy selected is one that has a transition temperature between 36° C. and 45° C. The temperature 36° C. is chosen because of the temperature of the human body; 45° C. is chosen because operating at higher temperatures could be destructive to body tissue, particularly some body proteins.

U.S. Pat. No. 4,991,602 to Amplatz et al., suggests a flexible guidewire made up of a shape memory alloy such as the nickel-titanium alloy known as nitinol. The guidewire is one having a single diameter throughout its midcourse, is tapered toward each end, and has a bead or ball at each of those ends. The bead or ball is selected to allow ease of movement through the catheter into the vasculature. The guidewire is symmetrical so that a physician cannot make a wrong choice in determining which end of the guidewire to insert into the catheter. The patent suggests that wound wire coils at the guidewire tip are undesirable. The patent further suggests the use of a polymeric coating (PTFE) and an anticoagulant. The patent does not suggest that any particular type of shape memory alloy or particular chemical or physical variations of these alloys are in any manner advantageous.

Examples of Ni—Ti alloys are disclosed in U.S. Pat. Nos. 3,174,851; 3,351,463; and 3,753,700.

Another catheter guidewire using Ni—Ti alloys is described in U.S. Pat. No. 5,069,226, to Yamauchi, et al. Yarnauchi et al. describes a catheter guidewire using a Ni—Ti alloy which additionally contains some iron, but is typically heat-treated at a temperature of about 400° to 500° C. so as to provide an end section which exhibits pseudo-elasticity at a temperature of about 37° C. and plasticity at a temperature below about 80° C. A variation is that only the end portion is plastic at the temperatures below 80° C.

U.S. Pat. No. 5,171,383, to Sagae, et al., shows a guidewire produced from a super-elastic alloy which is then subjected to a heat treatment such that the flexibility is sequentially increased from its proximal portion to its distal end portions. A thermoplastic coating or coil spring may be placed on the distal portion of the wire material. Generally speaking, the proximal end portion of the guidewire maintains a comparatively high rigidity and the most distal end portion is very flexible. The proximal end section is said in the claims to have a yield stress of approximately five to seven kg/mm$^2$ and an intermediate portion of the guidewire is shown in the claims to have a yield stress of approximately 11 to 12 kg/mm$^2$.

Published European Patent Application 0,515,201-A1 also discloses a guidewire produced at least in part of a super-elastic alloy. The publication describes a guidewire in which the most distal portion can be bent or curved into a desired shape by a physician immediately prior to use in a surgical procedure. Proximal of the guide tip, the guidewire is of a super-elastic alloy.

Published European Patent Application 0,519,604-A2 similarly discloses a guidewire which may be produced from a super-elastic material such as nitinol. The guidewire core is coated with a plastic jacket, a portion of which may be hydrophilic and a portion of which is not.

U.S. Pat. No. 5,213,111, to Cook et al., discloses a guidewire made using a composite guidewire core. The guidewire core consists of a tapered stainless steel wire surrounded by a layer of shape memory alloy such as a nickel titanium alloy. This composite guidewire core combines the properties of the ingredient materials.

European Patent EP 0359549 discloses a flexible cable constructed of a woven wire braid drawn snugly over the entire length of a metallic coil and then secured at the coil ends by welding or an adhesive. The patent suggests using this braided coil construction for wire guides in surgical devices.

PCT Application WO 092014508 discloses a guidewire which combines a tapered core wire with one or more coiled wires wrapped around the tapered distal portion of the core wire. In one of the described embodiments, the coiled wires are braided around the core wire to add torsional stability to the guidewire.

None of the above disclosures suggest the guidewire configuration described below.

SUMMARY OF THE INVENTION

This invention is a guidewire, preferably a guidewire suitable for introduction into the vasculature of the brain, and a method for its use. The guidewire desirably is of four particular components and may comprise others. The first component is a core wire of either a super-elastic alloy, a stainless steel, or a composite of both. The second component is a super-elastic ribbon braid which surrounds a portion of the flexible core wire and changes the mechanical properties of the device. The third component is an optional, but desirable, distally located coil of a soft and usually radio-opaque material terminated by an adhesive bead. The fourth component is a polymeric layer placed over some or all of the assembled metallic components which layer may be coated with an additional lubricious polymer coating.

The class of desirable super-elastic alloys includes Ni—Ti alloys and particularly those having specific physical characteristics, e.g., a stress-strain upper plateau at about 75±10 ksi and a lower plateau at 25±7.5 ksi (each measured at 3% strain) when the stress-strain relationship is measured to a strain of 6%.

A highly desirable variation of the inventive core wire comprises a long wire having a proximal section, a middle section, and a distal end section. The distal end section is typically the most flexible of the sections and is often at least about three centimeters long. The flexible distal end section may be partially tapered and covered by a coil assembly which is connected to the distal end of the guidewire at its distal tip using an, e.g., epoxy adhesive.

One desirable composite for use as the core involves a super-elastic alloy distal end section and a more proximal section or sections of another material or configuration, e.g., stainless steel wire or rod, stainless steel hypotube, super-elastic alloy tubing, etc.

The guidewire with its braided covering and distal coil may be coated or covered with a polymer layer. The layer may be used as-is or may serve as a "tie" layer to enhance its ability to traverse the lumen of the catheter. A lubricious polymer may be placed directly upon the tie layer. The tie layer may be a shrink-wrap tubing or a plasma deposition or may be a dip, spray, or fusion spray coating of an appropriate material. The tie layer may also be radio-opaque.

Ideally, there will be one or more radio-opaque markers placed upon the guidewire, e.g., at its distal tip and potentially along the length of the intermediate section. These markers may be used both to enhance the guidewire's radio-opacity and its ability to transmit torque from the proximal end to the distal end while maintaining a desired flexibility.

This invention also includes a catheter apparatus made up of the guidewire core and a thin-walled catheter designed to be advanced along the guidewire through the vasculature for positioning at a desired site.

DESCRIPTION OF THE INVENTION

Figures 1, 2, 3:
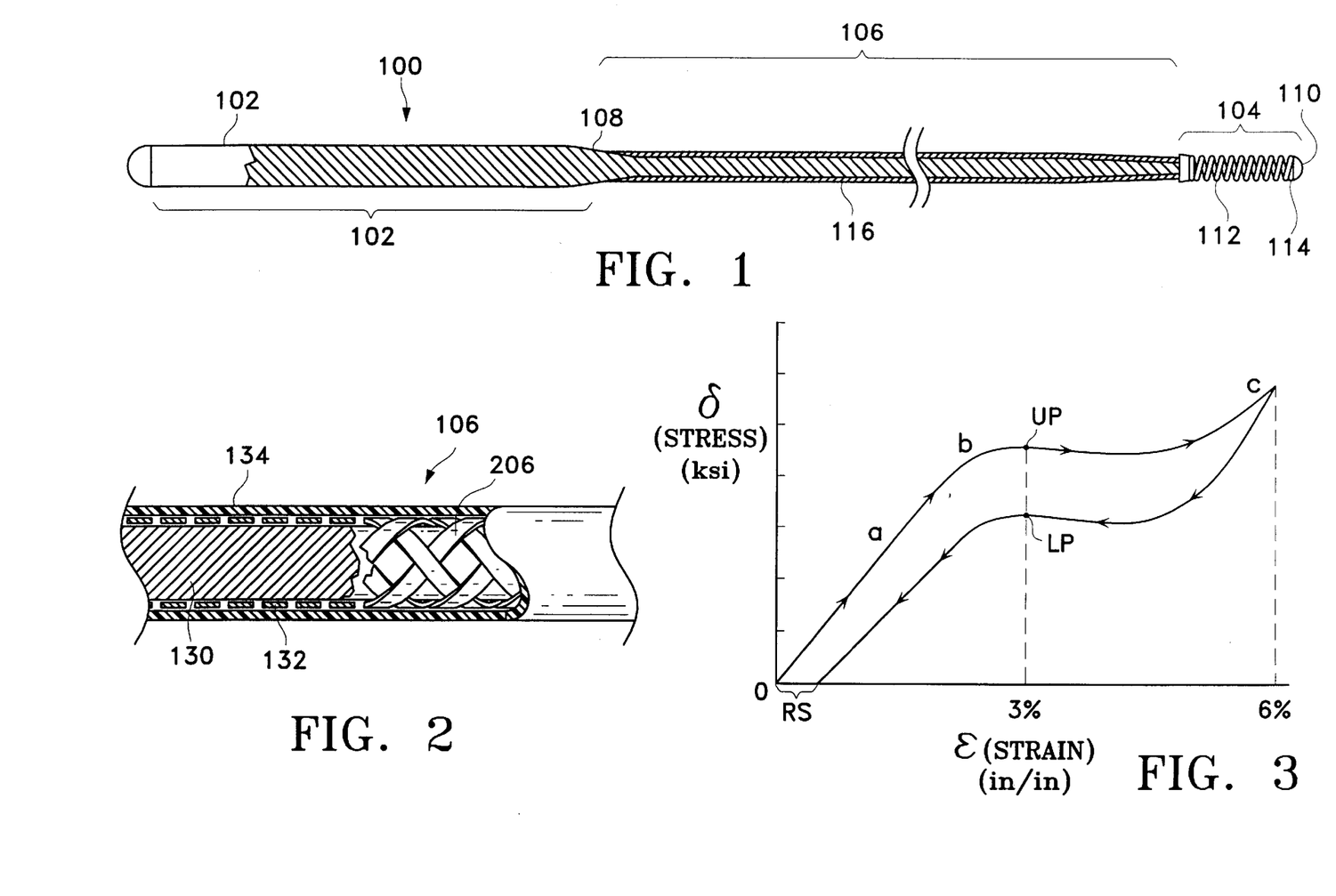
FIG. 1 shows a schematic side view (not to scale) of the major components of the inventive guidewire.
FIG. 2 is a partial cutaway side view of the inventive guidewire showing the braided covering over a portion of the middle section of the core wire and the polymeric external layer.
FIG. 3 shows a typical stress-strain diagram for a Ni—Ti alloy displaying objective criteria for selection of alloys for the inventive guidewire.

FIG. 1 shows an enlarged side view of a guidewire made according to the invention. The guidewire (100) is made up of the wire core formed of a flexible torqueable wire filament material and has a total length typically between about 50 and 300 centimeters. The proximal section of the core wire (102) preferably has a uniform diameter (along its length) of about 0.010 to 0.025 inches, preferably 0.010 to 0.018 inches. The relatively more flexible distal end section (104) extends for 3 to 30 centimeters or more of the distal end of the guidewire (100). A middle section (106) may have a diameter intermediate between the diameter of the two portions of the wire adjoining the middle section. The middle section (106) may be continuously tapered, may have a number of tapered sections or sections of differing diameters, or may be of a uniform diameter along its length. If the middle section (106) is of a generally uniform diameter, the core wire will neck down as is seen at (108). The distal end section (104) of the core wire typically has an atraumatic distal tip (110), a fine wire coil (112), and at least one adhesive joint (114). The fine wire coil (112) may be radio-opaque and made from materials including but not limited to platinum and its alloys. The atraumatic distal tip (110) may be radio-opaque to allow knowledge of the position of the coil (112) during the process of inserting the catheter and traversal of the guidewire through the vasculature.

At least some portion of the core wire—preferably the middle section (106)—has included thereon a braid. This braid is not seen in FIG. 1 but will be discussed in more detail below. The braid is constructed of a number of super-elastic ribbons.

All or part of the guidewire (100) is coated with one or more thin polymeric coating layers (116). The polymeric layers may be used as-is or as a layer for other polymers to enhance the lubricity of the assembly without adversely affecting the flexibility or shapeability of the guidewire. This invention includes portions or sections of the guidewire described above having the noted polymeric layer described below and an optional slippery, e.g., a hydrophilic, polymeric coating thereon. The innermost polymeric layer may be referred to as the "tie layer" while the outermost polymeric layer may be called an "outer layer coating." The mechanical properties of the guidewire may be varied through application of different tie layer coatings along differing sections of the guidewire, while varied outer layer coatings may be placed along sections of the guidewire to control frictional properties.

FIG. 2 shows a partial cutaway of the middle section of the inventive guidewire (106) showing the core wire (130), a supporting ribbon braid (132), and the polymeric covering (134). Not shown in FIG. 2 because it is only a very thin layer, is the optionally applied polymeric (often hydrophilic polymeric) outer layer coating exterior to the polymeric covering (134). As is noted elsewhere, single or multiple polymeric layers may be placed on any portion of the final guidewire assembly.

Guidewire Core

The inventive guidewire assembly is typically used in a catheter which is made up of an elongate tubular member having proximal and distal ends. The catheter is about 50 to 300 centimeters in length, typically between about 100 and 200 centimeters in length. Often, the catheter tubular member has a relatively stiff proximal section which extends along a major portion of the catheter length and one or more relatively flexible distal sections which provide greater ability of the catheter to track the guidewire through sharp bends and turns encountered as the catheter is advanced through the torturous paths found in the vasculature. The construction of a suitable catheter assembly having differential flexibility along its length is described in U.S. Pat. No. 4,739,768.

The materials used in the guidewires of this invention are alloys which exhibit super-elastic/pseudo-elastic shape recovery characteristics. These alloys are known. See, for instance, U.S. Pat. Nos. 3,174,851 and 3,351,463 as well as 3,753,700; the '700 patent describes a material because of the higher modulus of the material due to an increased iron content. These metals are characterized by their ability to be transformed from an austenitic crystal structure to a stress-induced martensitic (SIM) structure at certain temperatures, and return elastically to the austenitic structure when the stress is removed. These alternating crystalline structures provide the alloy with its super-elastic properties. One such well-known alloy, nitinol, is a nickel-titanium alloy. It is readily commercially available and undergoes the austenite-SIM-austenite transformation at a variety of temperature ranges between −20° C. and 30° C.

These alloys are especially suitable because of their capacity to elastically recover almost completely to the initial configuration once the stress is removed. Typically there is little plastic deformation, even at relatively high strains. This allows the guidewire to undertake substantial bends as it passes through the body's vasculature, and yet return to its original shape once the bend has been traversed without retaining any hint of a kink or a bend. Nevertheless, compared to similar stainless steel guidewires, less force need be exerted against the interior walls of the vessels to deform the guidewire of the invention along the desired path through the blood vessel thereby decreasing trauma to the interior of the blood vessel and reducing friction against the coaxial catheter.

To achieve these results of high strength and enhanced control even while allowing feedback to the attending physician during use, we have found that the following physical parameters of the alloy are suitable. In a stress-strain test as shown on a stress-strain diagram such as that found in FIG. 3 the stress found at the midpoint of the upper plateau (UP) (measured, e.g. at about 3% strain when the test end point is about 6% strain) should be in the range of 75 ksi (thousand pounds per square inch)±10 ksi and, preferably, in the range of 75 ksi±5 ksi. Additionally, this material should exhibit a lower plateau (LP) of 25±7.5 ksi, preferably 20±2.5 ksi, measured at the midpoint of the lower plateau. The material preferably has no more than about 0.25% residual strain (RS) (when stressed to 6% strain and allowed to return) and more preferably less than about 0.15% RS.

The preferred material is nominally 50.6%±0.2% Ni and the remainder Ti. The alloy should contain no more than about 500 parts per million of any of O, C, or N. These alloys often contain up to about 7% of one or more members of the iron group of metals, e.g., Fe, Cr, Co, etc. Typically such commercially available materials will be sequentially mixed, cast, formed, and separately cold-worked to 30–40%, annealed, and stretched.

By way of further explanation, FIG. 3 shows a stylized stress-strain diagram showing the various parameters noted above and their measurement on that diagram. As stress is initially applied to a sample of the material, the strain is at first proportional (a) until the phase change from austenite to martensite begins at (b). At the upper plateau (UP), the energy introduced with the applied stress is stored during the formation of the quasi-stable martensite phase or stress-induced-martensite (SIM). Upon substantial completion of the phase change, the stress-strain relationship again approaches a proportional relationship at (c). The stress is no longer applied when the strain reaches 6%. The measured value (UP) is found at the midpoint between zero and 6% strain, i.e., at 3% strain. If another terminal condition of strain is chosen, e.g., 7%, the measured valued of (UP) and (LP) would be found at 3.5%.

Materials having high UP values produce guidewires which are quite strong and allow exceptional torque transmission but cause a compromise in the resulting "straightness" of the guidewire. We have found that guidewires having high UP values in conjunction with high LP values are not straight. These guidewires are difficult to use because of their tendency to "whip" as they are turned. Again, that is to say, as a guidewire is turned it stores energy during as a twist and releases it quickly. The difficulty of using such a whipping guidewire should be apparent. Materials having UP values as noted above are suitable as guidewires.

Furthermore, materials having values of LP which are high, again, are not straight. Lowering the value of LP compromises the ability of the guidewire to transmit torque but improves the ease with which a straight guidewire may be produced. Lowering the LP value too far, however, results in a guidewire which, although round, has poor tactile response. It feels somewhat "vague" and "soupy" during its use. The LP values provided for above allow excellent torque transmission, straightness, and the valuable tactile response.

The values of residual strain discussed above define materials which do not kink or otherwise retain a "set" or configuration after stress during use as a guidewire.

In addition to the core wires made of super-elastic alloys, this invention also covers guidewire cores comprising various stainless steels. Suitable stainless steels include those typically used in medical devices, e.g., 304SS, 306SS, 312SS, and 316SS. Most preferred are 304SS and 316SS. In comparison to the guidewire cores made of super-elastic alloys, comparable stainless steel cores are more able to transmit torque and are typically stiffer. The trade-off is that stainless steels are much more likely to lack the elasticity of the super-elastic alloys.

Figure 4:
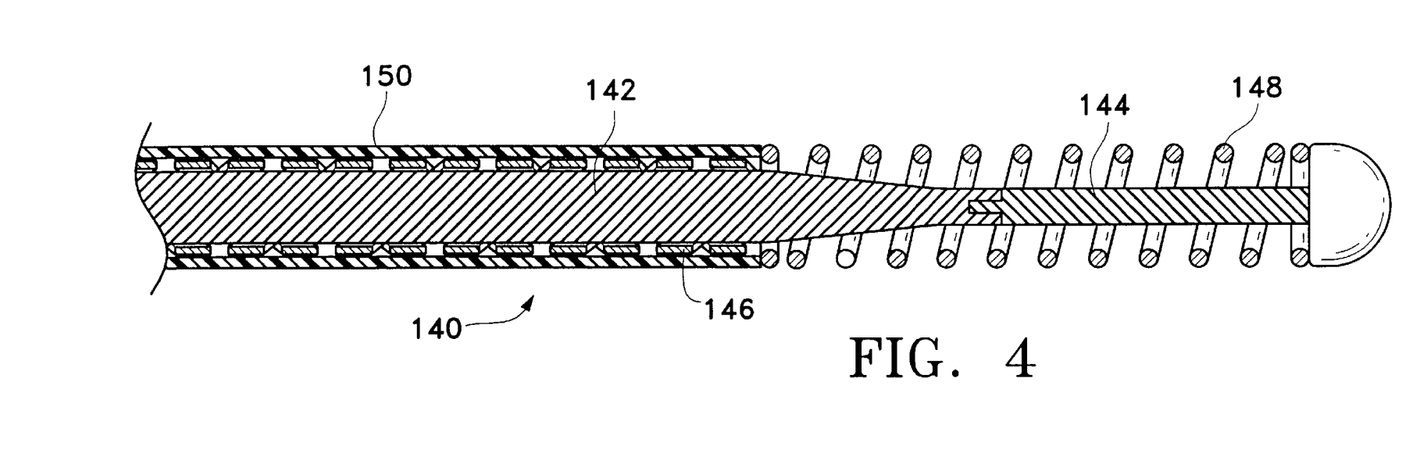
FIGS. 4 and 5 are partial cutaway side views showing various guidewire configurations made according to the invention.
Figure 5:
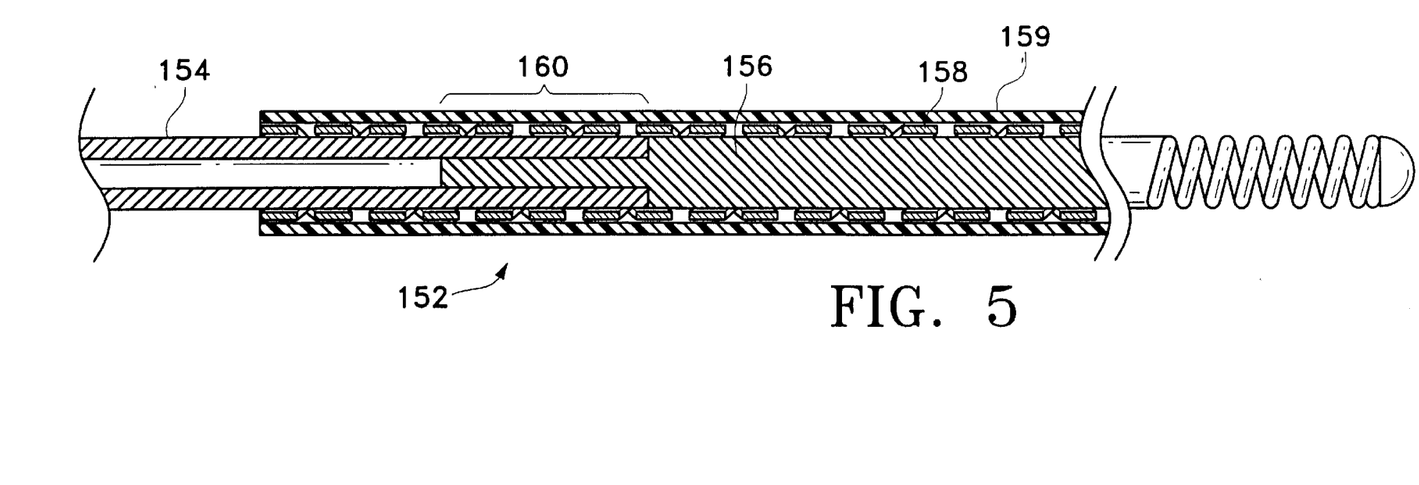

The core may be an assembly of components, or a composite, such as is shown in FIGS. 4 and 5. These figures depict only a few of the various arrangements contemplated under this invention. FIG. 4 shows a guidewire assembly (140) having a two-part composite core made up of a super-elastic alloy proximal portion (142) and a stainless steel distal section (144). The super-elastic braid (146) provides controlled mechanical support to the super-elastic core wire portion (142). A radio-opaque distal coil (148) and a polymeric covering (150) are also seen in the drawing. This combination of metallic components and the composite core wire has the following benefits: the small stainless steel distal section (144) is readily shapeable by a physician using the device; the radio-opaque coil (148) inhibits the guidewire section containing the small stainless steel distal section (144) from kinking and provides positional feedback; the super-elastic braided section (146) does not kink during the manipulation necessary to introduce the guidewire to the target site.

Another desirable variation of a composite core wire (152) is seen in FIG. 5. In this variation, the proximal section of the core wire (154) is stainless steel to provide proximal stiffness. A tubing member is depicted but a solid core member may be used with some provision for a joint to the adjoining super-elastic alloy section (156). An exterior braiding (158) is also shown over the depicted portion of the composite core wire (152). That braiding is made from a super-elastic alloy for kink resistance (particularly within the joint region (160)) and may be radio-opaque to allow observance of the guidewire during passage within the body. A polymeric covering (159) is also seen in the drawing.

This invention involves, in large part, the melding of the optimum qualities of the various physical parameters of the respective alloys to result in a guidewire assembly with greater overall effectiveness.

Figure 6A:
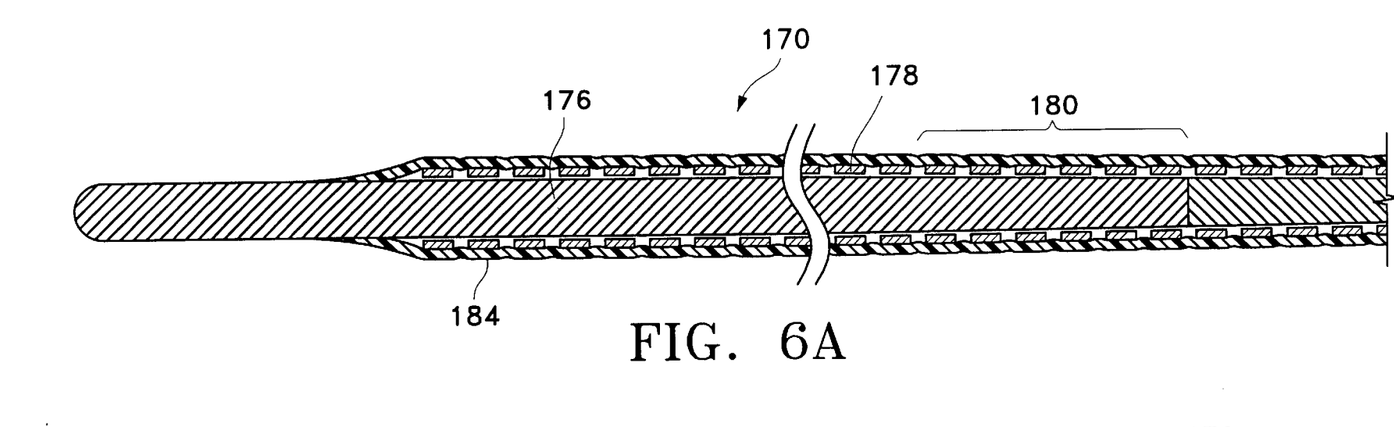
FIGS. 6A and 6B together form a partial cutaway side view of a preferred embodiment of the invention.
Figure 6B:
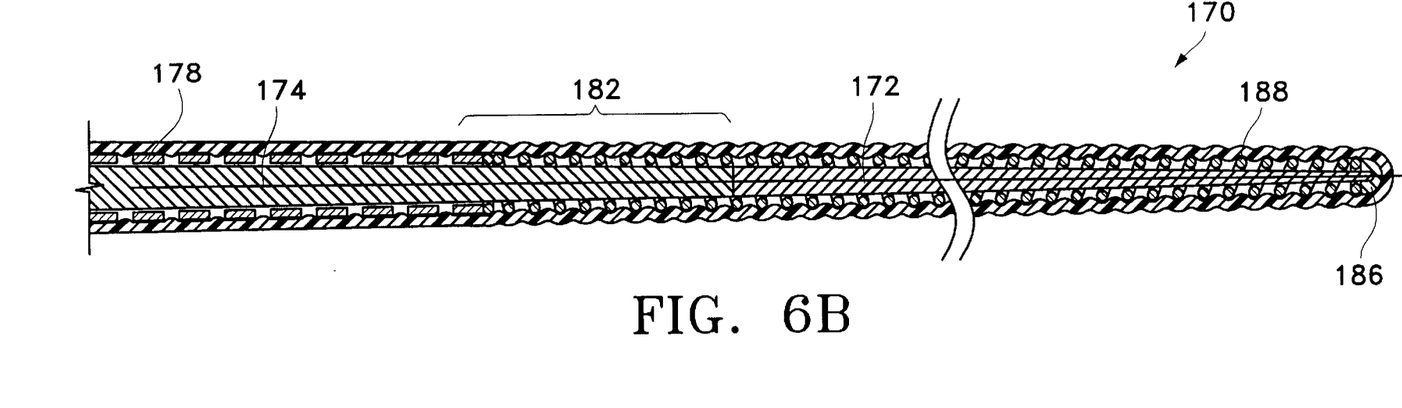

FIGS. 6A and 6B together depict a preferred embodiment of the invention. It is a guidewire including a composite core having sections of various alloys. Surrounding the composite core wire is a coil (188) over the distal end section (172), a super-elastic braid over the middle section (174), and a two-layer polymeric coating (184) covering both the distal end section (172) and the middle section (174).

Specifically, the depicted composite core wire is comprised of a stainless steel distal end section (172), a super-elastic alloy middle section (174), and a stainless steel proximal section (176). The stainless steel distal end section (172) allows the tip to be easily shaped by the user. The super-elastic middle section (174) of the guidewire core passes through a significant length of the most tortuous vasculature during a procedure and hence is the most significant candidate for a super-elastic alloy. The proximal section (176) is used primarily for pushing and for transmitting twisting ("torquing") motions between the proximal end and the distal end. Consequently, the choice for materials in the more-proximal end (176) is often stainless steel. If a more flexible path is to be accessed in the vasculature, the choice of materials for the more-proximal end (176) may be a super-elastic alloy.

Also depicted in the preferred embodiment of FIGS. 6A and 6B is a ribbon braid member (178) placed concentrically about the core wire in the middle section (174) and a portion of the middle section (176). The braid (178) need not cover the complete length of the core because only a portion requires the enhanced mechanical properties provided by the braid structure.

The core assembly depicted in FIGS. 6A and 6B is typical of guidewires used to access targets in the vasculature of the brain. It however is only "typical" and forms no critical portion of the invention. The core wire assembly has two tapering regions (180, 182) to help with the transition between various regions of the core. The core wire may taper for significant regions or over short distances. Such decisions are within the purview of the guidewire designer. Similarly, selection of a polymeric coating (184) is a matter of choice for the designer. The atraumatic distal tip (186) and radio-opaque coil (188) are relative common features on contemporary guidewires.

Braids

The braids used in this invention are exterior to the surface of the guidewire core and are used to provide specific physical strengths of various types, e.g., torsional rigidity, stiffness, kink resistance, composite elasticity, etc. The braid is placed directly upon the wire core and is bonded directly to the core wire body in at least two contact locations, and preferably distributively at multiple locations, with an adhesive.

Incomplete or distributive interfacial bonding between the core wire's cylindrical outer surface and the surrounding braid's tubelike inner surface produces a guidewire with greater flexibility than that which results from complete bonding at every potential interfacial contact point along the surfaces. As an illustration of the notion of incomplete interfacial bonding, one can use the analogy of an ordinary pencil device comprised of a shaft of lead surrounded by a hollow cylinder of wood. A pencil with complete interfacial bonding could be assembled by coating the entire lead in adhesive and placing it inside of the wooden cylinder; a pencil with incomplete interfacial bonding might be assembled after coating only the two ends of the lead with adhesive and leaving any other lead shaft surface area free of adhesive. Ordinary principles of engineering mechanics teach that the bending and torsional deflections of a shaft are inversely proportional to the effective radius of the cross section under a load. A guidewire with its core completely bonded to a surrounding braid will function more like a unified larger diameter shaft than will a incompletely bonded guidewire core and braid because of constraints on interfacial deflection imposed by the complete bonding. Thus a discontinuously bonded guidewire core and braid will resist bending or torsion deflection to a lesser degree and will consequently have greater overall flexibility under twisting or bending loads than will the same components assembled with complete interfacial bonding.

Although the braid (132) most desired is shown in FIG. 2 and has a single size of ribbon, the braid need not be so limited; multiple sizes of ribbon may be used as desired. The major limitations are simply the size, e.g., diameter, of the overall braid as finally constructed and the desired added stiffness to be added to the guidewire.

The braids typically useful in this invention comprise an even number of ribbons: one half of the ribbons wound one way, i.e., clockwise, and the remainder are wound the other way. A typical braid will be of eight to 16 ribbons. The braid may have a single pitch, an angle of a constituent ribbon measured against the axis of the braid, or it may have a pitch which varies along the axis of the braid.

Preferred super-elastic alloys include the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Commercial alloys containing up to about 8% of one or more other members of the iron group, e.g., Fe, Cr, Co, are considered to be encompassed within the class of super-elastic Ni/Ti alloys suitable for this service.

Metallic ribbons that are suitable for use in this invention are desirably between 0.25 mil and 3.5 mil in thickness and 2.5 mil and 12.0 mil in width. By the term "ribbon", we intend to include elongated shapes, the cross-section of which are not square or round and may typically be rectangular, oval or semi-oval. They should have an aspect ratio of at least 0.5 (thickness/width). In any event, for super-elastic alloys, particularly nitinol, the thickness and width may be somewhat finer, e.g., down to 0.25 mil and 1.0 mil, respectively. Currently available ribbons include sizes of 1 mil×3 mil, 1 mil×4 mil, 2 mil×6 mil, and 2 mil×8 mil.

The ribbons (206) making up the braid (132) shown in FIG. 2 may also contain a minor amount of non-super-elastic materials. Although metallic ribbons are preferred as the ancillary materials because of their strength-to-weight ratios, fibrous materials (both synthetic and natural) may also be used. Preferred, because of cost, strength, and ready availability are stainless steels (SS304, SS306, SS316, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radio-opacity.

Suitable non-metallic ribbons include high performance materials such as those made of polyaramids (e.g., KEVLAR) and carbon fibers.

The braids utilized in this invention may be made using commercially available tubular braiding machines. Whenever the term "braid" is used herein, we mean tubular constructions in which the ribbons making up the construction are woven in an in-and-out fashion as they cross to form a tubular member defining a single lumen. The braids may be made up of a suitable number of ribbons, typically six or more. Ease of production on a commercial braider typically results in braids having eight or sixteen ribbons.

The braid shown in FIG. 2 has a nominal pitch angle of 45°. Clearly the invention is not so limited. Other braid angles from 20° to 60° are also suitable. An important variation of this invention is the ability to vary the pitch angle of the braid either at the time the braid is woven or at the time the braid is included in the guidewire section or sections.

The braid (132) may be rough to the touch if not covered or further processed. Procedures such as rolling, sanding, or grinding may be used to smooth the surface of the braid if so desired. Removal of any produced particulates is, of course, necessary.

After such processing, the tubular braid (132) must be geometrically sized to surround a portion of the inventive core wire (130) within desired tolerances. When using a super-elastic alloy, the shaping step may also be desirable to preserve the integrity of the braided geometry. For instance, with a Cr-containing Ni/Ti super-elastic alloy which has been rolled into a 1×4 mil ribbon and formed into a 16-member braid, some heat treatment is desirable to maintain the braided structure's geometry and physical properties. Methods for sizing the tubular braid (132) to fit the core wire and preserve the braided geometry are an important aspect of the invention. We have found two effective methods for producing an interference fit between the tubular braid (132) and core wire (130) which employ heat and applied stress.

The first interference fitting method involves placing a core wire within a tubular braid to form an assembly, applying a tensile force to the braid along the longitudinal axis of the core wire to conform the braid to the core wire's geometry, heating the assembly to a temperature above 650 degrees Fahrenheit to possibly (but not necessarily) anneal the constituent ribbon, cooling the assembly to room temperature, and releasing the conforming tensile forces to produce an assembly with an interference fit.

The second interference fitting method involves placing a mandrel with the same geometry of a core wire into a tubular braid to form an assembly, applying a tensile force to the braid along the longitudinal axis of the core wire to conform the braid to the mandrel's geometry, heating the assembly to a temperature above 650 degrees Fahrenheit to possibly (but not necessarily) anneal the constituent ribbon, cooling the assembly to room temperature, releasing the conforming tensile forces, removing the sized braid from the mandrel, applying a compressive force to the braid along its longitudinal axis, placing the core wire within the compressed tubular braid to form an assembly, and releasing the compressive force to produce the desired interference fit. This method of interference fitting has the advantage of not subjecting the core wire to potential heating and cooling transformations during the sizing process.

Whether the outer surface of the braid (132) is smoothed or not, it is quite desirable to place an outer layer of a polymer on the exterior of the braiding. FIG. 2 depicts the use of that exterior tubing layer as a tie layer (134). This concept is discussed elsewhere herein. A thin layer of a hydrophilic polymeric is placed on the exterior of the tie layer (134). The hydrophilic polymeric layer is not depicted on the drawing because the layer is typically too thin to see. The tie layer (134) and its associated hydrophilic polymeric layer may be (but need not be) of the same composition throughout the resulting guidewire assembly.

Adhesive

An important concept in this invention is the use of an adhesive in the construction of the guidewire assembly both to adhere the tubular braid (132) to the core wire (130) and to form an atraumatic tip (110) on the most distal portion of the inventive guidewire assembly. The use of such epoxy adhesives provides two key advantages over other metal fastening methods such as soldering or welding.

First, epoxy adhesives do not require localized heating of the components to be fastened. The fastening regions on components to be welded or soldered often must reach very high temperatures to facilitate the flow of the welding or soldering material. These high temperatures can produce localized changes in material properties and strain patterns within the components which result in less desirable overall physical properties for the inventive device. Construction of the guidewire inventive guidewire assembly using an epoxy adhesive involves mixing the epoxy resin and hardener and applying it to the small contact surface between the two components to be fastened. This fastening may be conducted at room temperature, or at higher temperatures which may be desirable for shaping components such as the tubular braid.

Secondly, epoxy adhesives do not leave behind flux residues like those found on soldered or welded joints; there may be biocompatibility problems with such residues.

Of all the epoxy adhesives that are available, those which are biocompatible and adherent to the various metals of the guidewire assembly components are preferred. We have found that epoxy adhesives comprising bis-A epichlorohydrin resins and polyamine-polyamide hardeners, such as Tra-Bond FDA-2 (Tra-Con, Inc., Medford, Mass.) effectively meet the compatibility and structural demands of the inventive guidewire.

Guidewire Core Coatings

All or part of the guidewire core and braid may be covered or coated with one or more layers of a polymeric material. The coating is applied typically to enhance the mechanical properties of the guidewire assembly or the lubricity of the guidewire assembly during its traversal of the catheter lumen or the vascular walls. As noted above, both mechanical and frictional properties can be controlled by varying the inner and outer layer coating materials which may be applied to the metallic guidewire assembly.

Outer Layer Coating Materials

As noted above, at least a portion of the guidewire core and braid may be coated by dipping or spraying or by similar process with such materials as polysulfones, polyfluorocarbons (such as TEFLON), polyolefins such as polyethylene, polypropylene, polyesters (including polyamides such as the NYLON's and polyethyleneterephthalate), and polyurethanes; their blends and copolymers such as polyether block amides (e.g., PEBAX).

The guidewire core and braid may also be at least partially covered with other hydrophilic polymers including those made from monomers such as ethylene oxide and its higher homologs; 2-vinyl pyridine; N-vinylpyrrolidone; polyethylene glycol acrylates such as mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The polymeric coating may be cross-linked using various techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Polymers or oligomers applied using the procedure described below are activated or functionalized with photoactive or radiation-active groups to permit reaction of the polymers or oligomers with the underlying polymeric surface. Suitable activation groups include benzophenone, thioxanthone, and the like; acetophenone and its derivatives specified as:

where
$R^1$ is H, $R^2$ is OH, $R^3$ is Ph; or
$R^1$ is H, $R^2$ is an alkoxy group including —OCH$_3$, —OC$_2$H$_3$, $R^3$ is Ph; or
$R^1 = R^2 =$ an alkoxy group, $R^3$ is Ph; or
$R^1 = R^2 =$ an alkoxy group, $R^3$ is H; or
$R^1 = R^2 =$ Cl, $R^3$ is H or Cl.

Other known activators are suitable.

The polymeric coating may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The outer layer polymeric coating may be applied to the guidewire by any of a variety of methods, e.g., by spraying a solution or suspension of the polymers or of oligomers of the monomers onto the guidewire core or by dipping it into the solution or suspension. Initiators may be included in the solution or applied in a separate step. The guidewire may be sequentially or simultaneously dried to remove solvent after application of the polymer or oligomer to the guidewire and crosslinked.

The solution or suspension should be very dilute since only a very thin layer of polymer is to be applied. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

Particularly preferred as a coating for the guidewire cores discussed herein are physical mixtures of homo-oligomers of at least one of polyethylene oxide; poly 2-vinyl pyridine; polyvinylpyrrolidone, polyacrylic acid, polyacrylamide, and polyacrylonitrile. The catheter bodies or substrates are preferably sprayed or dipped, dried, and irradiated to produce a polymerized and crosslinked polymeric skin of the noted oligomers.

The lubricious hydrophilic coating is preferably produced using generally simultaneous solvent removal and crosslinking operations. The coating is applied at a rate allowing "sheeting" of the solution, e.g., formation of a visibly smooth layer without "runs". In a dipping operation for use with most polymeric substrates including those noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 50° C. to 125° C. Most preferred for the noted and preferred solvent systems is the range of 75° to 110° C.

Ultraviolet light sources may be used to crosslink the polymer precursors onto the substrate. Movement through an irradiation chamber having an ultraviolet light source at 90–375 nm (preferably 300–350 nm) having an irradiation density of 50–300 mW/cm$^2$ (preferably 150–250 mW/cm$^2$) for a period of three to seven seconds is desired. Passage of a guidewire core through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

We have found that frictional properties may be successfully controlled over the surface of a composite guidewire with different outer coating layers, depending upon the substrate to which they are applied. One preferred outer coating layer embodiment comprises hydrophilic outer coating layers over substrates of polyurethane, and TEFLON outer coating layers over all other substrates.

Tie Layers

We have found that it is often desirable to utilize the polymeric layer adjacent the core or braid as a "tie" layer for enhancement of the of an outer lubricious polymeric surface to the guidewire assembly. Of course, these materials must be able to tolerate the various other solvents, cleaners, sterilization procedures, etc. to which the guidewire and its components are placed during other production steps.

FIG. 2 shows a typical guide wire core section (100) made according to the invention having a metallic core (130), a braid (132), a polymeric tie layer (134), upon which a lubricious coating is placed.

Choice of materials for such tie layers is determined through their functionality. Specifically, the materials are chosen for their affinity or tenacity to the outer polymeric lubricious or hydrophilic coating. Clearly, the tie layer material must be flexible and strong. The tie layers may be placed onto the guidewire center in a variety of ways. The polymeric material may be extrudable and made into shrinkable tubing for mounting onto the guidewire through heating. It may be placed onto the guidewire core by dipping, spraying, shrink wrapping of polymeric tubing or other procedure. One quite desirable procedure involves the placement of a polymeric tubing of a fusible polymer, e.g., polyurethane, on the guidewire core which, in turn, is covered with a heat shrink tubing such as polyethylene. The outer tubing is shrunk down and the inner tubing is fused onto the guidewire core to form a tie layer. The tie layer is preferably 0.0004" to 0.003" in thickness. The melt temperature of the tie layer polymer desirably is appropriately chosen to fuse at the heat shrink temperature of the outer tubing. The outer shrink tubing is then simply peeled off, leaving the tie layer exposed for treatment with the lubricious coating.

We have found that various NYLON's, polyethylene, polystyrene, polyurethane, and polyethylene terephthalate (PET) make excellent tie layers. Preferred are polyurethane (Shore 80 A–55 D) and PET. Most preferred is polyurethane. It is additionally desirable to use a number of sections of polyurethane having differing hardnesses. For instance, the distal section may have a tie layer of Shore 80 A polyurethane; the proximal shaft might be Shore D55 polyurethane.

One preferred tie layer embodiment comprises higher durometer (40 D to 75 D) polyurethane layered over braided sections and lower durometer (60 A to 90 A) elastomeric grade polyurethane covering the more distal sections all the way to the distal tip. This tie layer embodiment, in combination with a tapered core wire below, provides a desired graduation of increasing flexibility along the length of the guidewire.

These polymeric tie layer materials may be formulated or blended to include radio opaque materials such as barium sulfate, bismuth trioxide, bismuth carbonate, tungsten, tantalum or the like.

As noted above, another manner of applying a tie layer is by heat-shrinking the tubing onto the braid. The guidewire core and the exterior braid is simply inserted into a tubing of suitable size—often with a small amount of a "caulking" at either end to seal the tubing. The tubing is cut to length and heated until it is sufficiently small in size. The resulting tubing tie layer desirably is between about 0.0005 and 0.015 inches in thickness. The thinner layers are typically produced from polyurethane or PET. The layer of lubricious polymer is then placed on the outer surface of the shrunk tubing.

Another procedure for preparing or pretreating guidewires prior to receiving a subsequent coating of a polymer, preferably a polymer which is lubricious, biocompatible, and hydrophilic, is via the use of a plasma stream to deposit a hydrocarbon or fluorocarbon residue. The procedure is described as follows: the guidewire core and braid is placed in a plasma chamber and cleaned with an oxygen plasma etch. It is then exposed to a hydrocarbon plasma to deposit a plasma-polymerized tie layer on the guidewire core to complete the pretreatment. The hydrocarbon plasma may comprise a lower molecular weight (or gaseous) alkanes such as methane, ethane, propane, isobutane, butane or the like; lower molecular weight alkenes such as ethene, propene, isobutene, butene or the like or; gaseous fluorocarbons such as tetrafluoromethane, trichlorofluoromethane, dichlorodifluoromethane, trifluorochloromethane, tetrafluoroethylene, trichlorofluoroethylene, dichlorodifluoroethylene, trifluorochloroethylene and other such materials. Mixtures of these materials are also acceptable. The tie layer apparently provides C—C bonds for subsequent covalent bonding to the outer hydrophilic polymer coating. Preferred flow rates for the hydrocarbon into the plasma chamber are in the range of 500 c.c./min. to for the hydrocarbon into the plasma chamber are in the range of 500 c.c./min. to 2000 c.c./min. and the residence time of the guidewire in the chamber is in the range of 1–20 minutes, depending on the chosen hydrocarbon and the plasma chamber operating parameters. Power settings for the plasma chamber are preferably in the range of 200 W to 1500 W.

A tie layer of plasma-produced hydrocarbon residue having a thickness on the order of $10\mu$ thick is disposed between braid and coating. This process typically produces layers of hydrocarbon residue less than about $1000\mu$ in thickness, and more typically less than about $100\mu$. The tie layer effectively bonds the outer layer to the guidewire core while adding very little additional bulk to the guidewire. Guidewires made according to this invention therefore avoid the size and maneuverability problems of prior art guidewires.

The pretreated guidewire may be coated with a polymer using a procedure such as described above. For example, the pretreated guidewire may be dipped in a solution of a photoactive hydrophilic polymer system, i.e., a latently photoreactive binder group covalently bonded to a hydrophilic polymer. After drying, the coated guidewire is cured by exposing it to UV light. The UV light activates the latently reactive group in the photoactive polymer system to form covalent bonds with crosslinked C—C bonds in the hydrocarbon residue tie layer. The dipping and curing steps are preferably repeated often enough, typically twice, to achieve the appropriate thickness of the hydrophilic coating layer.

One highly preferred variation of the invention involves a guidewire with metal core, preferably 0.010" to 0.025" diameter stainless steel or high elasticity alloy (such as nitinol) and a braid of stainless steel or a high elasticity alloy.

The guidewire may be cleaned by using an argon plasma etch in place of the oxygen plasma etch. The thickness of the plasma-polymerized tie layer may also vary without departing from the scope of this invention.

Although preferred embodiments of the present invention have been described, it should be understood that various changes, adaptations, and modifications may be made therein without departing from the spirit of the invention and the scope of the claims which follow.

We claim as our invention:

1. A guidewire suitable for guiding a catheter within a body lumen, comprising:
   a) an elongated flexible wire core having a proximal section, a middle section, a distal end section,
   b) a coil covering at least a portion of said distal end section and bonded to said end section distally with an adhesive,
   c) a tubular super-elastic alloy braid covering at least a portion of said middle section and bonded to said wire core in at least two locations with an adhesive, and
   d) a polymeric layer covering extending at least over said middle section and said distal end section.

2. The guidewire of claim 1 wherein the core comprises a super-elastic alloy.

3. The guidewire of claim 2 wherein the super-elastic alloy comprises a nickel and titanium alloy.

4. The guidewire of claim 1 wherein the core comprises a stainless steel.

5. The guidewire of claim 1 wherein at least the middle section comprises a super-elastic alloy.

6. The guidewire of claim 5 wherein the super-elastic alloy comprises a nickel and titanium alloy.

7. The guidewire of claim 1 wherein at least the middle section comprises a stainless steel.

8. The guidewire of claim 1 wherein at least the distal end section comprises a super-elastic alloy.

9. The guidewire of claim 8 wherein the super-elastic alloy comprises a nickel and titanium alloy.

10. The guidewire of claim 1 wherein at least the distal end section comprises a stainless steel.

11. The guidewire of claim 1 wherein the coil comprises a super-elastic alloy.

12. The guidewire of claim 11 wherein the super-elastic alloy comprises nickel and titanium.

13. The guidewire of claim 1 wherein the coil comprises a stainless steel.

14. The guidewire of claim 1 wherein the super-elastic tubular braid comprises a nickel and titanium alloy.

15. The guidewire of claim 1 wherein the adhesive comprises an epoxy.

16. The guidewire of claim 15 wherein the epoxy comprises a high-temperature bis-A epichlorohydrin epoxide resin and polyamine-polyamide hardener.

17. The guidewire of claim 1 wherein the polymeric layer comprises at least one of NYLON, polyethylene, polystyrene, polyurethane, and polyethylene terephthalate.

18. The guidewire of claim 17 wherein the layer comprises polyethylene terephthalate or polyurethane.

19. The guidewire of claim 18 wherein the layer is polyurethane.

20. The guidewire of claim 17 wherein at least a portion of the polymeric layer is coated w/a lubricious polymeric material.

21. The guidewire of claim 20 wherein the lubricious polymeric material comprises at least one hydrophilic polymer.

22. The guidewire of claim 17 wherein the polymeric layer additionally comprises a radio-opaque material selected from barium sulfate, bismuth trioxide, bismuth carbonate, tungsten, and tantalum.

23. The guidewire of claim 1 wherein the guidewire additionally comprises an atraumatic distal tip comprising epoxy.

24. The guidewire of claim 1 additionally comprising a catheter sheath.

25. A guidewire suitable for guiding a catheter within a body lumen comprising:
   a) an elongated flexible wire core having a proximal section, a middle section, a distal end section,
   b) a coil covering at least a portion of said distal end section and bonded to said end section distally with an adhesive,
   c) a tubular super-elastic alloy braid covering at least a portion of said middle section and fastened to said wire core by incomplete interfacial bonding with an adhesive, and
   d) a polymeric layer covering extending at least over said middle section and said distal end section.

26. The guidewire of claim 25 wherein the core comprises a super-elastic alloy.

27. The guidewire of claim 26 wherein the super-elastic alloy comprises a nickel and titanium alloy.

28. The guidewire of claim 25 wherein the core comprises a stainless steel.

29. The guidewire of claim 25 wherein at least the middle section comprises a super-elastic alloy.

30. The guidewire of claim 29 wherein the super-elastic alloy comprises a nickel and titanium alloy.

31. The guidewire of claim 25 wherein at least the middle section comprises a stainless steel.

32. The guidewire of claim 25 wherein at least the distal end section comprises a super-elastic alloy.

33. The guidewire of claim 32 wherein the super-elastic alloy comprises a nickel and titanium alloy.

34. The guidewire of claim 25 wherein at least the distal end section comprises a stainless steel.

35. The guidewire of claim 25 wherein the coil comprises a super-elastic alloy.

36. The guidewire of claim 35 wherein the super-elastic alloy comprises nickel and titanium.

37. The guidewire of claim 25 wherein the coil comprises a stainless steel.

38. The guidewire of claim 25 wherein the super-elastic tubular braid comprises a nickel and titanium alloy.

39. The guidewire of claim 25 wherein the adhesive comprises an epoxy.

40. The guidewire of claim 39 wherein the epoxy comprises a high-temperature bis-A epichlorohydrin epoxide resin and polyamine-polyamide hardener.

41. The guidewire of claim 25 wherein the polymeric layer comprises at least one of NYLON, polyethylene, polystyrene, polyurethane, and polyethylene terephthalate.

42. The guidewire of claim 41 wherein the layer comprises polyethylene terephthalate or polyurethane.

43. The guidewire of claim 42 wherein the layer is polyurethane.

44. The guidewire of claim 41 wherein at least a portion of the polymeric layer is coated w/a lubricious polymeric material.

45. The guidewire of claim 44 wherein the lubricious polymeric material comprises at least one hydrophilic polymer.

46. The guidewire of claim 41 wherein the polymeric layer additionally comprises a radio-opaque material selected from barium sulfate, bismuth trioxide, bismuth carbonate, tungsten, and tantalum.

47. The guidewire of claim 25 wherein the guidewire additionally comprises an atraumatic distal tip comprising epoxy.

48. The guidewire of claim 25 additionally comprising a catheter sheath.

49. A guidewire suitable for guiding a catheter within a body lumen, comprising:
   a) an elongated flexible wire core,
   b) a tubular super-elastic alloy braid covering at least a portion of said wire core and fastened to said wire core by incomplete interfacial bonding with an adhesive, and
   c) a polymeric layer covering extending at least over said tubular super-elastic alloy braid.

50. The guidewire of claim 49 wherein the core comprises a super-elastic alloy.

51. The guidewire of claim 50 wherein the super-elastic alloy comprises a nickel and titanium alloy.

52. The guidewire of claim 49 wherein the core comprises a stainless steel.

53. The guidewire of claim 49 wherein the super-elastic tubular braid comprises a nickel and titanium alloy.

54. The guidewire of claim 49 wherein the adhesive comprises an epoxy.

55. The guidewire of claim 54 wherein the epoxy comprises a high-temperature bis-A epichlorohydrin epoxide resin and polyamine-polyamide hardener.

56. The guidewire of claim 49 wherein the polymeric layer comprises at least one of NYLON, polyethylene, polystyrene, polyurethane, and polyethylene terephthalate.

57. The guidewire of claim 56 wherein the layer comprises polyethylene terephthalate or polyurethane.

58. The guidewire of claim 57 wherein the layer is polyurethane.

59. The guidewire of claim 56 wherein the polymeric layer additionally comprises a radio-opaque material selected from barium sulfate, bismuth trioxide, bismuth carbonate, tungsten, and tantalum.

60. The guidewire of claim 49 wherein at least a portion of the polymeric layer is coated w/a lubricious polymeric material.

61. The guidewire of claim 60 wherein the lubricious polymeric material comprises at least one hydrophilic polymer.

62. The guidewire of claim 49 additionally comprising a catheter sheath.

63. The guidewire of claim 49 wherein the core comprises a composite of a stainless steel and a super-elastic alloy.

64. The guidewire of claim 63 wherein the super-elastic alloy comprises a nickel and titanium alloy.

65. The guidewire of claim 49 wherein the guidewire additionally comprises an atraumatic distal tip comprising an epoxy.

* * * * *

UNITED STATES PATENT AND TRADEMARK OFFICE

CERTIFICATE OF CORRECTION

PATENT NO. : 5,827,201

DATED : October 27, 1998

INVENTOR(S) : SAMSON et al.

It is certified that error appears in the above-identified patent and that said Letters Patent is hereby corrected as shown below:

*Column 3, line 21*: please change " Yarnauchi " to -- Yamauchi --.

Signed and Sealed this

Twenty-third Day of March, 1999

Attest:

Q. TODD DICKINSON

Attesting Officer

Acting Commissioner of Patents and Trademarks